United States Patent
Kang et al.

(10) Patent No.: US 9,895,370 B2
(45) Date of Patent: Feb. 20, 2018

(54) PHARMACEUTICAL COMPOSITION FOR PREVENTING OR TREATING OF CIRRHOSIS OF LIVER COMPRISING G PROTEIN COUPLED RECEPTOR 119 LIGAND AS AN ACTIVE INGREDIENT

(71) Applicants: DONGGUK UNIVERSITY INDUSTRY—ACADEMIC COOPERATION FOUNDATION, Seoul (KR); SEOUL NATIONAL UNIVERSITY R&DB FOUNDATION, Seoul (KR)

(72) Inventors: Keon Wook Kang, Seoul (KR); Kyeong Lee, Goyang-si (KR); Jin Won Yang, Seoul (KR)

(73) Assignee: PHARMEDIX.CO., LTD, Seoul (KR)

( * ) Notice: Subject to any disclaimer, the term of this patent is extended or adjusted under 35 U.S.C. 154(b) by 0 days.

(21) Appl. No.: 15/355,376

(22) Filed: Nov. 18, 2016

(65) Prior Publication Data
US 2017/0143714 A1    May 25, 2017

(30) Foreign Application Priority Data

Nov. 19, 2015  (KR) .................. 10-2015-0162521
Nov. 14, 2016  (KR) .................. 10-2016-0150990

(51) Int. Cl.
*A61K 31/506*  (2006.01)
*A61K 31/4545*  (2006.01)

(52) U.S. Cl.
CPC ........ *A61K 31/506* (2013.01); *A61K 31/4545* (2013.01)

(58) Field of Classification Search
CPC ........................... C07D 417/14; C07D 413/14
See application file for complete search history.

(56) References Cited

U.S. PATENT DOCUMENTS

| | | | | |
|---|---|---|---|---|
| 6,060,494 A | * | 5/2000 | Faasch ................ | C07D 261/18 514/378 |
| 2010/0190750 A1 | * | 7/2010 | Chu ...................... | A61K 31/00 514/64 |
| 2017/0049773 A1 | * | 2/2017 | Kang .................... | A61K 31/506 |

FOREIGN PATENT DOCUMENTS

| | | | |
|---|---|---|---|
| KR | 101086040 B1 | | 11/2011 |
| KR | 10-2014-0008368 | * | 1/2014 |
| KR | 10-2015-0010771 | * | 1/2015 |
| WO | WO 2015111971 A1 | * | 7/2015 ......... A61K 31/4545 |

OTHER PUBLICATIONS

U. Shah et al., 27 RSC Drug Discovery Series, 177-214 (2012).*
J. Polli et al., 43 Xenobiotica, 498-508 (2013).*
S.U. Kang et al., 18 Drug Discovery Today, 1309-1315 (2013).*
D.J. Nunez et al., 9 PLoS One, 1-15 (2014).*
J.W. Wang et al., The FASEB Journal (2016).*
N. Pham, 21 Bioorganic & Medicinal Chemistry, 1349-1356 (2013).*
M. Sakairi et al., Chemistry & Pharmaceutical Bulletin.*
A. Planagumà et al., 19 The FASEB Journal, 1120-1122 (2017).*
S. Yoshida et al., 13 Diabetes, Obesity and Metabolism, 34-41 (2011).*
Z-L Chu et al., 24 Molecular Endocrinology, 161-170 (2010).*
English-Language Machine Translation of KR10-2014-0008368 (2014).*
English-Language Machine Translation of KR10-2015-0010771 (2015).*
Final Rejection issued in U.S. Appl. No. 15/302,228 (dated Oct. 17, 2017).*
Non-Final Rejection issued in U.S. Appl. No. 15/302,228 (dated Jul. 13, 2017).*
Lee et al., Diabetes & Metabolism Journal, 2012, 36, 262-267.*
Lan et al., British Journal of Pharmacology, 2012, 165, 2799-2807.*
Jin Won Yang, "Inhibition of hepatic steatosis and fibrosis by GPR119", Doctorate Thesis, Nov. 18, 2015. (116 Pages).

* cited by examiner

*Primary Examiner* — Alexander R Pagano
(74) *Attorney, Agent, or Firm* — Lucas & Mercanti, LLP

(57) ABSTRACT

Provided is a pharmaceutical composition for preventing or treating liver fibrosis, comprising a GPR119 ligand as an active ingredient. The composition comprising the GPR119 ligand as an active ingredient significantly inhibits the expression of collagen I, transforming growth factor β (TGFβ) and α-smooth muscle actin (α-SMA), thereby inhibiting HSC activation, and also significantly inhibits HSC proliferation. Therefore, the composition may be effectively applied in improvement, prevention, inhibition or treatment of liver fibrosis.

7 Claims, 15 Drawing Sheets

PHARMACEUTICAL COMPOSITION FOR PREVENTING OR TREATING OF CIRRHOSIS OF LIVER COMPRISING G PROTEIN COUPLED RECEPTOR 119 LIGAND AS AN ACTIVE INGREDIENT

STATEMENT REGARDING ANY GOVERNMENT SPONSORED RESEARCH OR DEVELOPMENT

The present invention was undertaken with the support of Open Translational Research Center for Innovative Drug (OTRCID) No. 2012M3A9C1053532 grant funded by the Ministry of Science, ICT and Future Planning.

CROSS-REFERENCE TO RELATED APPLICATIONS

The application claims priority to and the benefit of Korean Patent Application No. 10-2015-0162521, filed on Nov. 19, 2015, and Korean Patent Application No. 10-2016-0150990, filed on Nov. 14, 2016, the disclosures of which are incorporated herein by reference in their entirety.

FIELD OF THE INVENTION

The present invention relates to a pharmaceutical composition for preventing or treating liver fibrosis, and more particularly, to a pharmaceutical composition for preventing or treating liver fibrosis, which comprises a G protein-coupled receptor 119 (GPR119) ligand as an active ingredient.

BACKGROUND OF THE INVENTION

Liver fibrosis refers to a condition in which damaged liver tissue is modified into fiber tissue such as collagen without repair to normal liver cells as part of adaptive responses of the body, which are accompanied with toxic materials or various infectious, immune and metabolic diseases. In particular, it has been known that hepatic stellate cells (HSCs) transformed into myofibroblasts are proliferated and transferred to produce excessive connective tissue, leading to fibrosis of the liver. While the liver fibrosis is the adaptive response occurring in the body during repair of the damaged tissue, liver failure seems inevitable in that the liver is substituted by fiber tissue that cannot perform the unique functions of the liver such as metabolism in the body and bile secretion. When the liver fibrosis is consistently repeated, it develops into liver cirrhosis and leads to death. Therefore, development of a suitable therapeutic agent is the key task for the development of a new drug.

Currently, the development of a therapeutic agent for liver fibrosis has focused on whether a drug is able to inhibit the activity of HSCs, and as the conventional drug described above, penicillamine, 16,16-dimethyl prostaglandin E2, biphenyl dimethyl dicarboxylate, colchicine, glucocorticoid, malotilate, gamma interferon, pentoxifylline, pyridine-2,4-dicarboxylic-diethylamide or pyridine-2,4-dicarboxylic-di(2-methoxyethyl)amide are known (see Korean Patent No. 10-1086040). However, since these drugs have little effect or severe side effects, as of now, there is no effective therapeutic agent for liver fibrosis.

The human GPR119 gene is located on the X chromosome, and consists of a single exon. The human GPR119 gene has a different genetic composition from that of a mouse or rat, and there is a high similarity in expressed proteins between a human and a mouse. Like other receptors in the G protein-coupled receptor family, the human GPR119 has 7 transmembrane domains, but G proteins interacting therewith in cells have not yet been clearly identified.

It is known that GPR119 receptors are mainly present in pancreatic beta cells, and small intestinal enteroendocrine cells, for example, K cells and L cells. In the pancreas, GPR119 activation is known to increase cAMP levels using intracellular adenylate cyclase as a second messenger, and thus enhances insulin secretion by external glucose stimulation. Insulin stimulation is a glucose-dependent reaction, and thus the GPR119 receptor does not induce hypoglycemia, which is the disadvantage of the conventional therapeutic agent for diabetes. It has been reported that, in the small intestine, GPR119 activation stimulates secretion of GLP-1, GLP-2 and peptide YY from the L cells, and secretion of an insulinotropic peptide (GIP) from the K cells, and all of the GPR119 actions described above may predict the mechanism of anti-diabetes efficacy in response to a signal for stimulating a decrease in blood sugar level. It has been reported that, in practice, in an in vivo experiment using a mouse, administration of the GPR119 ligands effectively improves an insulin tolerance test (ITT) and a glucose tolerance test (GTT).

As endogenous GRP119 ligands, human lipid-like materials [N-acyl ethanolamines (NAEs) such as OEA, PEA and LEA] are used, and it has been reported that they have affinity to receptors such as PPAR alpha and TRPV1, as well as GPR119. Synthetic GPR119 ligands have been manufactured by large pharmaceutical companies including Arena Pharmaceuticals, GlaxoSmithKline (GSK), etc. Most of the synthetic GPR119 ligands are highly likely to be next generation therapeutic agents for diabetes, and particularly, MBX2982 and GSK1292263 are the most advanced materials entering phase II clinical trials.

According to conventional research, GPR119 expression in the liver was rarely found, and thus the efficacy of the GPR119 ligand on liver fibrosis had never been evaluated.

SUMMARY OF THE INVENTION

The present invention is provided to solve the conventional technical problems described above, and suggests that a GPR119 ligand may be suitably applied in prevention or treatment of liver fibrosis by disclosing that a ligand acting on the GPR119 receptor has an excellent therapeutic effect on liver fibrosis.

However, technical problems to be solved in the present invention are not limited to the above-described problems, and other problems which are not described herein will be fully understood by those of ordinary skill in the art from the following description.

To achieve this goal, the present invention provides a pharmaceutical composition for preventing or treating liver fibrosis, which comprises a GPR119 (G protein coupled receptor 119) ligand as an active ingredient.

In one exemplary embodiment of the present invention, the GPR119 ligand may be 4-((4-(1H-tetrazol-1-yl)phenoxy)methyl)-2-(1-(5-ethylpyrimidin-2-yl)piperidin-4-yl) thiazole (MBX2982) or 3-isopropyl-5-(4-(((6-(4-(methylsulfonyl)phenyl)pyridin-3-yl)oxy)methyl)piperidin-1-yl)-1,2,4-oxadiazole (GS K1292263).

In another exemplary embodiment of the present invention, the GPR119 ligand may inhibit HSC proliferation.

In still another exemplary embodiment of the present invention, the GPR119 ligand may inhibit HSC activation.

In yet another exemplary embodiment of the present invention, the GPR119 ligand may enhance the activity of AMP-activated protein kinase (AMPK).

In yet another exemplary embodiment of the present invention, the GPR119 ligand may inhibit collagen I expression.

In yet another exemplary embodiment of the present invention, the GPR119 ligand may inhibit the expression of transforming growth factor β (TGFβ).

In yet another exemplary embodiment of the present invention, the GPR119 ligand may inhibit the expression of α-smooth muscle actin (α-SMA).

A composition comprising a GPR119 ligand as an active ingredient according to the present invention significantly inhibits collagen I, transforming growth factor β (TGFβ) and α-smooth muscle actin (α-SMA), thereby inhibiting HSC activation and also significantly inhibiting HSC proliferation. Therefore, the composition according to the present invention can be effectively applied in improvement, prevention, inhibition or treatment of liver fibrosis.

DETAILED DESCRIPTION OF THE INVENTION

Figure 1A:
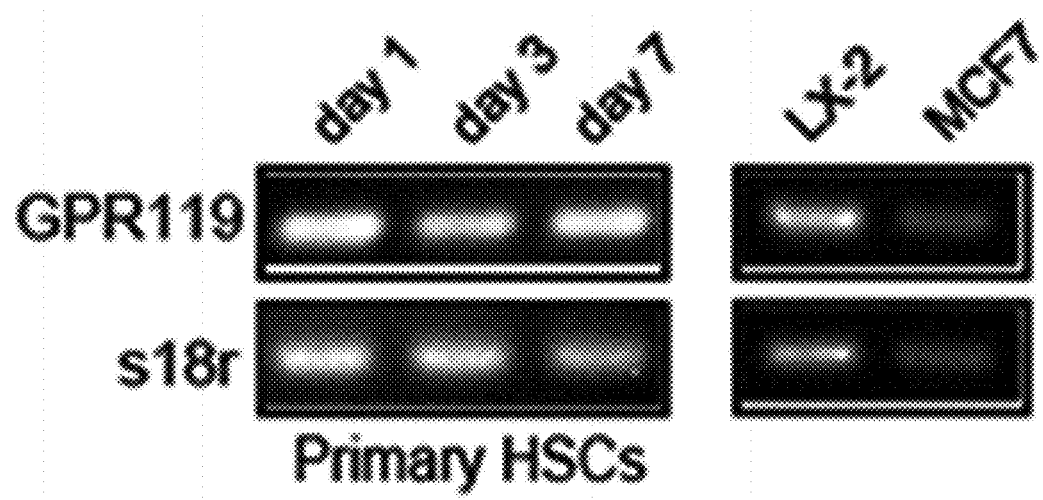
FIG. 1a illustrates mRNA expression of GPR119 in mouse HSCs.

The inventors found that a GPR119 ligand, which is in development as an anti-diabetes therapeutic agent, may inhibit HSC activation and proliferation to exhibit excellent effects in the treatment of liver fibrosis, and as a signaling system for the GPR119 ligand is identified, may be suitably used in treatment of liver fibrosis, and based on this, the present invention was completed.

Hereinafter, the present invention will be described in detail.

The present invention provides a pharmaceutical composition for preventing or treating liver fibrosis, comprising a GPR119 ligand as an active ingredient.

The GPR119 ligand may be, but is not limited to, 4-((4-(1H-tetrazol-1-yl)phenoxy)methyl)-2-(1-(5-ethylpyrimidin-2-yl) piperidin-4-yl)thiazole (MBX2982) or 3-isopropyl-5-(4-(((6-(4-(methylsulfonyl)phenyl)pyridin-3-yl)oxy) methyl)piperidin-1-yl)-1,2,4-oxadiazole (GSK1292263), may be commercially available or synthesized, and can be any material which binds to the GPR119 receptor to enhance the expression of the receptor.

The inventors confirmed GPR119 expression in HSCs activated by liver fibrosis induction, and observed the effect of a GPR119 ligand on HSC activation to identify the functional role of GPR119 in HSCs.

In one exemplary embodiment of the present invention, it was confirmed that, when HSCs were treated with a GPR119 ligand, expression of collagen I, transforming growth factor β (TGFβ) and α-smooth muscle actin (α-SMA) was significantly inhibited, thereby inhibiting HSC activation (see Examples 2 and 3).

In another exemplary embodiment of the present invention, to identify a signaling mechanism for the inhibition of liver fibrosis by a GPR119 ligand, a GPR119 signaling pathway, cyclic AMP/Protein kinase A (cAMP/PKA), was activated, and thus it was confirmed that the GPR119 ligand enhances AMP-activated protein kinase (AMPK) (see Example 4).

In still another exemplary embodiment of the present invention, an inhibitory effect of the GPR119 ligand on HSC proliferation was investigated, and thus it was confirmed that HSC proliferation was inhibited by the treatment with the GPR119 ligand (see Example 5).

Therefore, the GPR119 ligand inhibits HSC activation, and also inhibits HSC proliferation, and thus liver fibrosis may be improved, prevented or treated.

The composition of the present invention may further comprise one or more of the known active ingredients having a therapeutic effect for liver fibrosis, as well as the GPR119 ligand.

The composition of the present invention may further comprise a suitable carrier, excipient and diluent, which are conventionally used in preparation of a pharmaceutical composition. Also, the composition may be used in dosage forms including an oral form such as powder, a granule, a tablet, a capsule, a suspension, an emulsion, a syrup, or an aerosol, a drug for external use, a suppository, or a sterilized injectable solution according to a conventional method suitable for each form.

Carrier, excipients and diluents which can be included in the composition may be lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinyl pyrrolidone, water, methylhydroxybenzoate, propylhydroxybenzoate, talc, magnesium stearate and mineral oil. The composition may be formulated with a filler, a thickening agent, a binder, a wetting agent, a dispersant, a diluent such as a surfactant or an excipient, which is conventionally used.

A solid formulation for oral administration may be a tablet, pill, powder, granule or capsule, and such a solid formulation may be prepared by mixing at least one excipient, for example, starch, calcium carbonate, sucrose, lactose and gelatin, with the active ingredient. Also, in addition to the simple excipient, lubricants such as magnesium stearate and talc may also be used. As a liquid formulation for oral administration, a suspension, a liquid for internal use, an emulsion, or a syrup may be used, and a generally-used simple diluent such as water or liquid paraffin, as well as various types of excipients, for example, a wetting agent, a sweeter, a fragrance and a preservative may be included. A formulation for parenteral administration includes a sterilized aqueous solution, a non-aqueous solvent, a suspension, an emulsion, a lyophilizing agent and a suppository. As the non-aqueous solvent or suspension, propylene glycol, polyethylene glycol, a vegetable oil such as olive oil, or an injectable ester such as ethyl oleate may be used. As a suppository base, Witepsol, Tween 61, cacao butter, laurin fat, or glycerogelatin may be used.

The term "administration" used herein refers to providing a predetermined composition to an individual by a suitable method.

A preferable dosage of the pharmaceutical composition of the present invention may be determined according to a condition and body weight of an individual, severity of a disease, a drug form, an administration route, and duration, by one of ordinary skill in the art. For preferable effects, the GPR119 ligand of the present invention may be administered at 0.1 to 100 mg/kg, and preferably, 1 to 30 mg/kg once a day or several times a day.

The pharmaceutical composition of the present invention may be administered to an individual by various routes. All of the administration routes may be expected, and the pharmaceutical composition may be administered by, for example, oral, rectal or intravenous, intramuscular, subcutaneous, uterine septum or intracerebrovascular injection. The pharmaceutical composition of the present invention is determined according to the type of active ingredient, in addition to various related parameters such as a disease to be treated, an administration route, a patient's age, sex and body weight, and the severity of a disease.

In addition, the pharmaceutical composition of the present invention may be used for prevention and treatment of liver fibrosis independently or in combination with surgery, hormone treatment, drug treatment and methods using biological response modifiers.

EXAMPLES

Hereinafter, to help in understanding the present invention, exemplary embodiments will be disclosed. However, the following examples are merely provided to more easily understand the present invention, and the scope of the present invention is not limited to the examples.

Solutions and Methods

A. Preparation of Reagents and Materials

AMP-activated protein kinase (AMPK), phospho-AMPK, p-Smad2, p-Smad3, Smad2, Smad3, acetylated lysine, lamin A/C, horseradish peroxidase-conjugated donkey anti-rabbit IgG, and horseradish peroxidase-conjugated donkey anti-mouse IgG antibody were purchased from Cell Signaling Technology (Beverly, Mass., USA). Anti-collagen I antibodies were provided by Abcam plc. (Cambridge, Mass., USA). p300, c-Myc, and anti-goat IgG antibodies were purchased from Santa Cruz Biotechnology (Dallas, Tex., USA). Smooth muscle Ab-1 antibodies were purchased from Sigma (St. Louis, Mo., USA). Anti-glyceraldehyde 3-phosphate dehydrogenase (GAPDH) antibodies, H-89, and compound C were provided by Calbiochem (San Diego, Calif., USA). MBX-2982 was manufactured by Medchem Express (Monmouth County, N.J., USA).

B. Animal Test

Preparation of Laboratory Animals 6-week-old male C57BL/6J mice (Joongang laboratory animal, Seoul) were acclimated in a laboratory environment for 1 week with solid feed, and randomly arranged in control groups and experimental groups according to randomized block design. Then, carbon tetrachloride (1 ml/kg) was administered to 6-week-old male C57BL/6 mice (Joongang laboratory animal, Seoul) twice a week for three weeks to induce liver fibrosis, and a GPR119 ligand (10 mg/kg) suspended in 40% PEG400 was orally administered thereto once a day for five days per week. For liver fibrosis models induced by dimethylnitrosamine (DMN), DMN (10 mg/kg) was administered to mice three times a week to induce liver fibrosis. As the control group, a vehicle-treated group was used. After termination of the experiment, the laboratory animals were fasted for 12 hours or more, and anesthetized with Zoletil to obtain blood and the liver, and the liver was washed with 0.1 M phosphate buffered saline (PBS; pH 7.4) and weighed. The blood obtained from the abdominal aorta was centrifuged in an SST tube at 3000×RPM for 20 minutes to isolate the serum.

Biochemical Analysis Methods for Blood and Liver Tissue

For the above-mentioned laboratory animals, serum alanine transaminase (ALT), aspartate transaminase (AST), total bilirubin (T-BIL) and direct bilirubin (D-BIL) were analyzed using an automated hematology analyzer, Spectrum [(Abbott Laboratories, Abbott Park, Ill.)].

Sirius Red Staining

The liver samples obtained as described above were prepared into sections, and the tissue section was fixed with 10% buffered neutral formalin and embedded in paraffin. Afterward, the resulting section was sliced to a 4-μm thickness, and put on a slide to fix a specimen, stained with sirius red, and observed using an optical microscope.

Confirmation of Protein Expression in Tissue Using Western Blot

A predetermined amount of liver tissue was homogenized in a mortar with liquid nitrogen and a lysis buffer, and the resulting tissue solution was transferred into a new tube and then vortexed. The tissue solution was centrifuged at 14,000 rpm and 4° C. for 20 minutes, and the intermediate layer was extracted to quantify a protein by a Bradford method. 30 μg of proteins were analyzed by electrophoresis using an SDS polyacrylamide gel, and the change of protein expression was analyzed by western blot.

Isolation and Confirmation of RNA in Tissue Using Trizol Method 1 mL of a Trizol solution per 0.1 g of the liver tissue was added to disrupt tissue, and then centrifuged at 4° C. and 12,000×g for 10 minutes. The supernatant was transferred into a new tube, 200 μl of chloroform was added thereto, and then vortexed. The supernatant was transferred into a new tube, and mixed with isopropanol at a 1:1 ratio. Following vigorous stirring for 15 seconds and maintaining at room temperature for 10 minutes, the resulting mixture was centrifuged at 12,000×g and 4° C. for 10 minutes to remove the supernatant, and the remaining precipitate was treated with 1 ml of 70% ethanol and centrifuged at 7,500×g and 4° C. for 5 minutes. Following the removal of the ethanol, a tube containing an RNA precipitate was dried at room temperature for 5 minutes, and an RNA pellet was lysed with nuclease-free water. A concentration of the extracted RNA sample was measured at 260 nm and 280 nm using a UV/VIS spectrometer (Nanodrop, Thermo, U.S.A.), cDNA was synthesized using an RT kit, and then the change of mRNA expression was confirmed by real time PCR.

C. Isolation and Culture of HSCs from Mice

HSCs were isolated from a male C57BL/6 mouse, a male GPR119 WT mouse and a GPR119 KO mouse. More specifically, each mouse was anesthetized to perform an abdominal incision, a cannula was inserted into the hepatic portal vein to introduce a gas mixture of 5% $CO_2$ and 95% $O_2$, and then $Ca^{2+}$, $Mg^{2+}$-free Hank's balanced salt solution was injected into the cannula at 37° C. to remove blood in the liver. Afterward, a 0.1% collagenase type IV (Sigma, U.S.A.) solution was injected. The liver tissue was detached from the body and prepared in a liver cell suspension, and following centrifugation at 1000×g for 10 minutes, a precipitated cell layer was obtained by floating HSCs to isolate through a density gradient method using Nycodenz. The isolated HSCs were cultured in high glucose Dulbecco's Modified Eagle's Medium (DMEM) containing 10% fetal bovine serum, 50 U/ml penicillin and 50 mg/ml streptomycin at 37° C. in 5% $CO_2$.

D. Culture of Human HSC Line (LX-2)

A human HSC line (LX-2, Milipore, U.S.A.) was plated in a 6-well plate, and grown to confluency in DMEM supplemented with 1% penicillin-streptomycin (Hyclone, U.S.A.) and 2% fetal bovine serum (Hyclone, U.S.A.) at 37° C. in a 5% $CO_2$ incubator. For a further experiment, the confluent HSC line was incubated in an FBS-free medium, instead of the 2% FBS-added medium.

E. Human Tissue Sample

A liver cancer tissue sample donated by a liver cancer patient who had received surgery to remove cancer in Chosun University Hospital and a peripheral normal tissue sample were used. Experimental protocols followed the ethical guidelines of the 1975 Declaration of Helsinki, the procedures were conducted with consent of all patients, and approved by IRB (CHOSUN 2013-04-005).

F. Cell Fractionation

A whole cell lysate and a nuclear fraction were separated according to a conventional method. More specifically, the whole cell lysate was obtained by lysing cells washed with phosphate buffered saline (PBS) with a lysis buffer [10 mM Tris-HCl (pH 7.1), 100 mM NaCl, 1 mM EDTA, 10% glycerol, 0.5% Triton X-100, 0.5% Nonidet P-40, 1 mM dithiothreitol and 0.5 mM phenylmethylsulfonyl fluoride (PMSF)] at 4° C. for 30 minutes, and centrifuging the resulting solution at 14,000×g for 15 minutes to obtain a supernatant. To obtain the nuclear fraction, a low-osmotic pressure buffer containing 10 mM HEPES (pH 7.9), 10 mM KCl, 0.1 mM EDTA, 1 mM DTT and 0.5 mM PMSF was added and reacted at 4° C. for 10 minutes. Following addition of 10% Nonidet P-40 and vortexing for 10 seconds, the supernatant obtained by centrifugation at 13,000 rpm for 3 minutes was removed, and the remaining precipitate was washed three times with a low-osmotic pressure buffer. The precipitate was mixed with a high-osmotic pressure buffer [20 mM HEPES (pH 7.9), 400 mM NaCl, 1 mM EDTA, 1 mM DTT and 1 mM PMSF] and vortexed again at 4° C. for 10 minutes to induce a reaction for 20 minutes. Following centrifugation at 13,000 rpm for 10 minutes, a supernatant was obtained to be used as a nuclear fraction. A protein concentration was quantified using a protein quantify kit of PRO-MEASURE™ protein measurement solution (iNtRON Biotechnology, South Korea) according to the Bradford assay.

G. Isolation of Total RNA and RT-PCR and Real-Time RT-qPCR Analyses

Total RNA (1 mg) extracted from cells using Trizol and a Maxime RT PreMix Kit (iNtRON Biotechnology, Gyeonggi-do, Korea) was used to obtain cDNA. For RT-PCR, a target gene was amplified by PCR using a Maxime™ PCR PreMix Kit according to the manufacturer's instructions, and subjected to electrophoresis in a 2% agrose gel, thereby identifying the amplified PCR product. Here, the specific sequence information of primers used herein is shown in Table 1.

TABLE 1

| Type | | Sequence (5'-3') | |
|---|---|---|---|
| mouse GPR119 | F | TGTCCTAACCATCCTCATCA | (SEQ ID NO: 1) |
| | R | ATAGCCACGCCAATCAAG | (SEQ ID NO: 2) |
| mouse S18 ribosomal protein (mouse S18r) | F | GTAACCCGTTGAACCCCATT | (SEQ ID NO: 3) |
| | R | CCATCCAATCGGTAGTAGCG | (SEQ ID NO: 4) |
| human GPR119 | F | GGCTGTGGTTAGTGTCTTAC | (SEQ ID NO: 5) |

TABLE 1-continued

| Type | | Sequence (5'-3') |
|---|---|---|
| | R | ACGAAGTGAGGGTGAAATAC (SEQ ID NO: 6) |
| human S16 ribosomal protein (human S16r) | F | TCCAAGGGTCCGCTGCAGTC (SEQ ID NO: 7) |
| | R | CGTTCACCTTGATGAGCCCATT (SEQ ID NO: 8) |

Meanwhile, for real-time RT-qPCR, the synthesized cDNA was assessed in a CFX Connect™ Real-Time PCR Detection System (Bio-Rad Laboratories, CA, USA) instrument using a SYBR green dye (Bio-Rad). The CP value of the gene was calibrated with the CP value of S 18r gene. Also, through a melting curve analysis, specificity of the amplified PCR product was confirmed. The specific sequence information of primers used herein is shown in Table 2.

TABLE 2

| Type | | Sequence (5'-3') |
|---|---|---|
| mouse S18 ribosomal protein (S18r) | F | GTAACCCGTTGAACCCCATT (SEQ ID NO: 3) |
| | R | CCATCCAATCGGTAGTAGCG (SEQ ID NO: 4) |
| mouse col1A1 | F | ACTGCAACATGGAGACAGGTCAGA (SEQ ID NO: 9) |
| | R | ATCGGTCATGCTCTCTCCAAACCA (SEQ ID NO: 10) |
| mouse TGFβ1 | F | CTTCAGCTCCACAGAGAAGAACTGC (SEQ ID NO: 11) |
| | R | CACGATCATGTTGGACAACTGCTCC (SEQ ID NO: 12) |
| human TGFβ1 | F | CCCAGCATCTGCAAAGCTC (SEQ ID NO: 13) |
| | R | GTCAATGTACAGCTGCCGCA (SEQ ID NO: 14) |
| human col1A1 | F | AACATGACCAAAAACCAAAAGTG (SEQ ID NO: 15) |
| | R | CATTGTTTCCTGTGTCTTCTGG (SEQ ID NO: 16) |
| rat TGFβ1 | F | TCGGGAGAGAGGAGGACTTTG (SEQ ID NO: 17) |
| | R | GGCTTGCGACCCACGTAGTA (SEQ ID NO: 18) |
| rat GAPDH | F | AGATCCACAACGGATACATT (SEQ ID NO: 19) |
| | R | TCCCTCAAGATTGTCAGCAA (SEQ ID NO: 20) |

H. Western Blot

Sodium dodecylsulfate-polyacrylamide gel electrophoresis (SDS-PAGE) was performed using a gel electrophoresis device (Mighty Small SE 250, Hoefer Scientific Instruments, San Francisco) according to the method established by the inventors. A lysed cell fraction was diluted with a sample dilution buffer [63 mM Tris (pH. 6.8), 10% glycerol, 2% SDS, 0.0013% bromophenol blue, 5% β-mercaptoethanol], and subjected to electrophoresis in an electrode buffer (15 g Tris, 72 g glycerin and 5 g SDS contained in an 1 L solution) using a 8-12% gel. After electrophoresis, the gel was transferred to a nitrocellulose membrane to transfer proteins using an electrophoresis device for transfer in a transfer buffer (25 mM Tris, 192 mM glycerin, 20% v/v methanol (pH. 8.3)] at 40 mA for 3 hours. The nitrocellulose membrane was reacted with first antibodies, reacted with horseradish peroxidase-conjugated goat anti-rabbit IgG and horseradish peroxidase-conjugated goat anti-mouse IgG as secondary antibodies for 1 hour, and visualized using an ECL chemiluminescence system (Amersham, Gaithesberg, Mass.).

I. Transduction

Plasmids were transduced into approximately 50-70% confluent cells using a FuGENE HD reagent (Roche, Nutley, N.J.) in a cell culture flask containing TOM (Hyclone) medium. Plasmids were added to the cells using 3 ml of a FuGENE HD reagent and 1 ml of TOM medium per mg of the plasmids to induce transduction for approximately 6 hours. To calibrate the total amount of the transduced plasmids, plasmids (mock-transduction) only having the backbone of an overexpressed plasmid were transduced into cells of the control group. Following the transduction, the resulting cells were stabilized in a culture medium for 18 hours, and then treated with a drug.

J. Reporter Gene Analysis

A reporter gene assay was performed using a dual-luciferase reporter assay system (Promega, Madison, Wis.). Cell lines were cultured, and luciferase construct-transfected cells were transduced with a Fugene HD reagent. After the experiment was terminated, the cells were lysed, and an activity was analyzed using the Luminoskan.

K. Immunoprecipitation

Total fraction protein was reacted with corresponding antibodies at 4° C. for 12 hours or more. An antigen-antibody conjugate was reacted with protein G-agarose at 4° C. for 2 hours to precipitate, and then reacted with 2× Laemmli buffer. The extracted protein was observed by an immunochemical method.

L. Chromatin Immunoprecipitation (ChIP) Analysis

A chromatin fragment was extracted using an EZ-ChIP™ kit (Merck Millipore Corporation; Darmstadt, Germany). Formaldehyde was directly added to treated cells in a culture flask to have a final concentration of 1% at room temperature for 10 minutes, thereby fixing the cells, and the cells were washed with phosphate buffered saline (PBS). The cells were lysed in 50 mM Tris-HCl (pH 8.1) containing 1% SDS and 10 mM EDTA by sonication, and centrifuged at 10,000 g for 10 minutes to obtain a cell extract solution. The cell extract solution was diluted with 10-fold ChIP dilution buffer [Tris-HCl (16.7 mM, pH 8.1), 167 mM NaCl, 1.2 mM EDTA, 0.01% SDS and 1.1% Triton X-100], and protein A-agarose was added to remove non-specific reactants. A 10% solution was separately dispensed and stored to be used as an input control. The resulting cells were reacted with 1 mg of antibodies or preimmune IgG at 4° C. for 12 hours, and additionally immunoprecipitated with protein A-agarose beads for 2 hours. The precipitated antigen-antibody conjugate was washed, and a chromatin-antigen-antibody complex which had been fixed was dissociated at 65° C. for 4 hours by adding 5M NaCl to have a final concentration of 200 mM. DNA was extracted by phenol-chloroform extraction, and a chromatin fragment was amplified by real time-qPCR. As specific primers for a p300-binding site in a human colla1 promoter, primers shown in Table 3 were used.

TABLE 3

| Type | | Sequence (5'-3') | |
|---|---|---|---|
| p300 | F | CATTCCCAGCTCCCCTCTCT | (SEQ ID NO: 21) |
|  | R | AGTCTACGTGGCAGGCAAGG | (SEQ ID NO: 22) |

EXAMPLES

Example 1. Examination of GPR119 Expression in HSCs

Since various receptors for free fatty acids and lipid derivatives were expressed in cells present in the liver, GPR119 expression in HSCs activated in induction of liver fibrosis was analyzed.

More specifically, mouse HSCs isolated and cultured by method C were analyzed by conventional PCR according to method G, and as shown in FIG. 1a, when analysis was performed on day 1, 3 and 7, which are activation steps induced by in vitro culture of the mouse HSCs, mRNA expression of GPR119 was observed from the first day. Also, in the human breast cancer cell line MCF7, which is reported to express GPR119, and the human HSC line LX-2, cultured by method D, mRNA expression of GPR119 was confirmed by PCR, as shown in FIG. 1a.

Figure 1B:
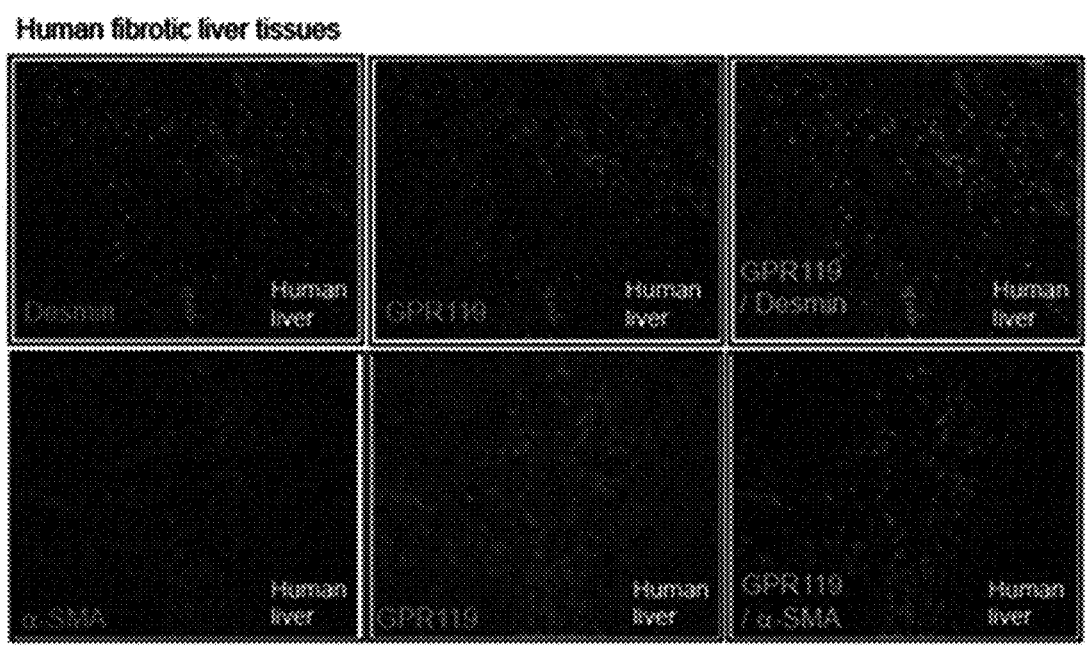
FIG. 1b illustrates GPR119 expression in liver fibrosis tissue derived from human liver cancer tissue.

Additionally, GPR119 expression in liver fibrosis tissue derived from the human liver cancer tissue obtained by method E was observed through immunohistochemical staining, which showed that, as shown in FIG. 1b, GPR119 was expressed in HSCs in the fibrotic tissue.

Example 2. Examination of Inhibitory Effect of GPR119 Ligand on HSC Activation

To identify the functional role of GPR119 in HSCs, the effect of a GPR119 ligand on HSC activation was observed.

Figure 2A:
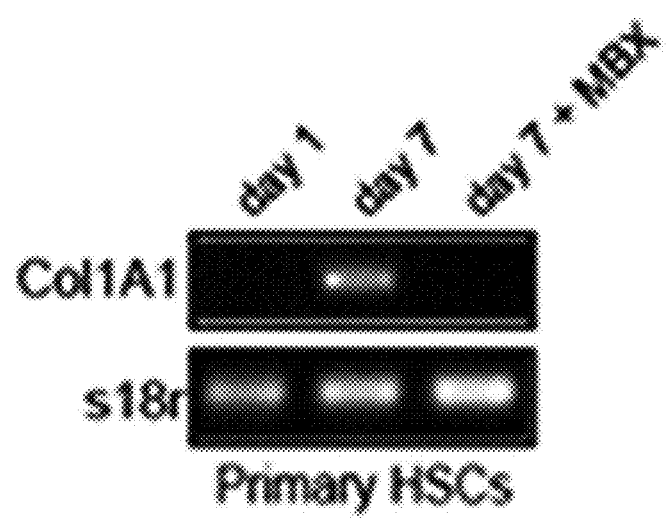
FIG. 2a illustrates the change of mRNA expression of col1A1 during treatment with a GPR119 ligand in mouse HSCs.

First, the change of mRNA expression of collagen collA1, induced in an in vitro culture-induced activation step of the primary cultured HSCs isolated from the mouse liver according to method C was observed. Consequently, as shown in FIG. 2a, HSCs were in vitro cultured and simultaneously treated with a GPR119 ligand (MBX-2982) on day 1, 3, and 5, repeatedly, thereby confirming that the mRNA expression of collagen collA1 was considerably inhibited.

Figure 2B:
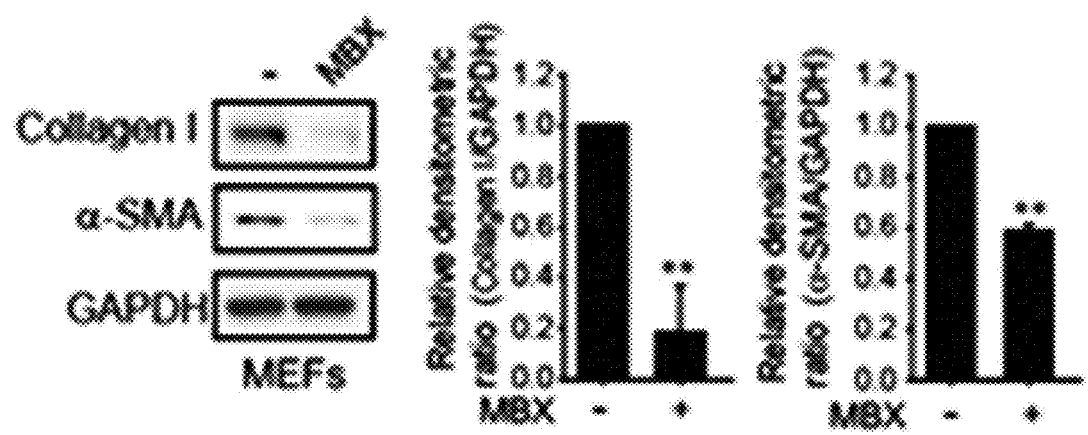
FIG. 2b illustrates the changes of collagen I and α-SMA expression according to the treatment with a GPR119 ligand in mouse embryonic fibroblasts (MEFs)

Subsequently, the change of protein expression of a marker, α-smooth muscle actin (α-SMA), for collagen I basally (?) expressed in mouse embryonic fibroblasts (MEFs) and HSCs activated by the treatment with a GPR119 ligand (MBX-2982), was assessed by the method described in H, which showed that, as shown in FIG. 2b, collagen I and α-SMA expression in the MEFs was inhibited by the treatment with the GPR119 ligand (MBX-2982).

Figure 2C:
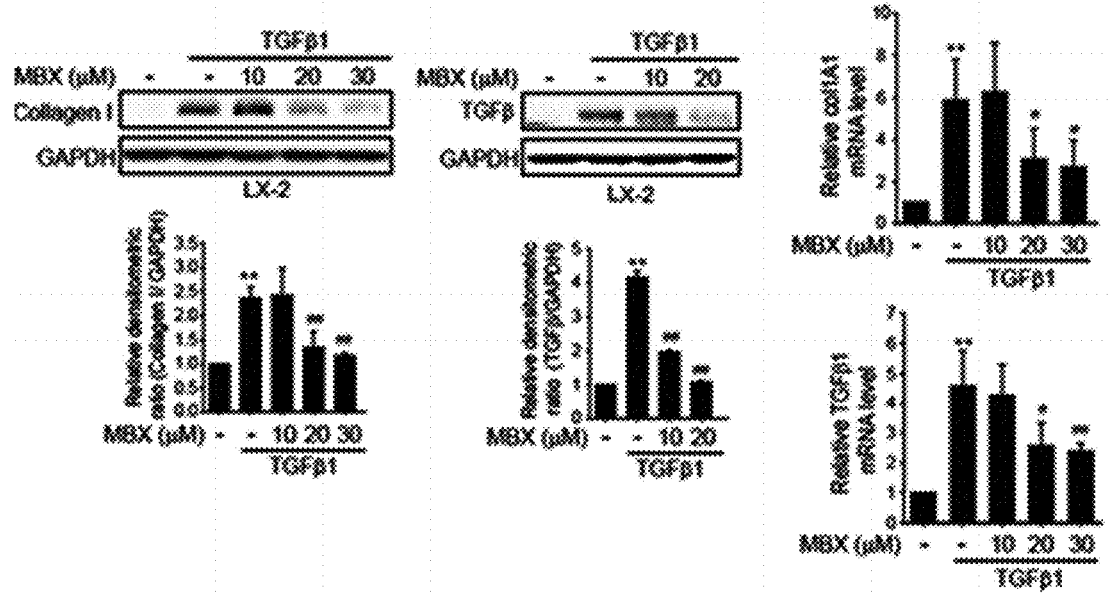
FIG. 2c illustrates the changes of mRNA expression of TGFβ1-inducible collagen I and TGFβ proteins according to the treatment with a GPR119 ligand (MBX-2982) in a human liver cell line LX-2.
Figure 2D:
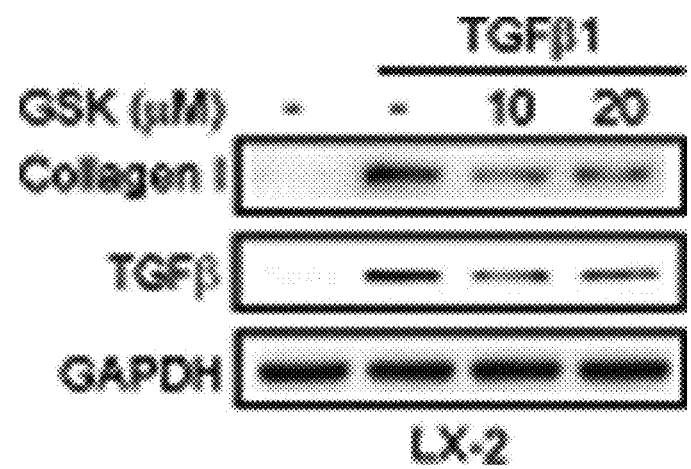
FIG. 2d illustrates inhibition of collagen synthesis and inhibition of TGFβ expression by treatment with a GPR119 ligand (GSK1292263) in a human liver cell line LX-2.

A critical cytokine having an influence on the induction of liver fibrosis, TGFβ1, is a potent fibrosis stimulation factor for HSCs. To examine the expression of a liver fibrosis-inducing factor which was increased when the human liver cell line LX-2, cultured by method D was treated with TGFβ1, changes in expression according to the treatment with GPR119 ligands (MBX-2982, GSK1292263) were assessed by the methods described in G and H, thereby observing the effect of the GPR119 ligands. Consequently, as shown in FIGS. 2c and 2d, when the GPR119 ligands (MBX-2982, GSK1292263) were treated, mRNA expression of TGFβ1-inducible collagen I and TGFβ protein was inhibited.

Figure 2E:
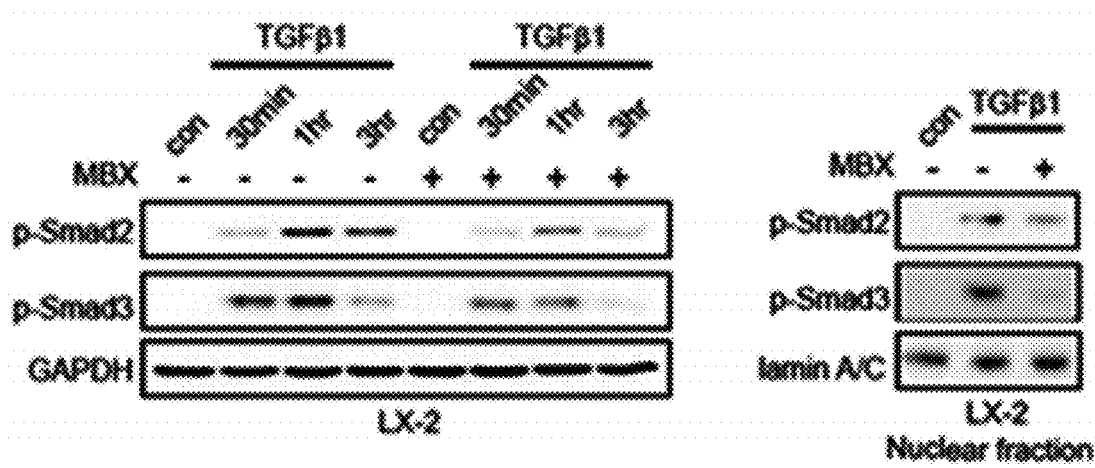
FIG. 2e illustrates the change of Smad2/Smad3 expression by treatment with a GPR119 ligand in a human liver cell line LX-2.

Thereafter, the change of the expression of a fibrosis-inducing signaling pathway, Smad2/Smad3, elevated by TGFβ1 in the human liver cell line LX-2, according to the GPR119 ligand (MBX-2982) treatment was assessed by the method described in H. Consequently, as shown in FIG. 2e, when the GPR119 ligand (MBX-2982) was treated, it was confirmed that phosphorylation and nuclear translocation of the fibrosis-inducing signaling pathway, Smad2/Smad3, elevated by TGFβ1 were inhibited.

Example 3. Examination of Effect of GPR119 Ligand on Inhibiting Liver Fibrosis

To examine improvement of liver fibrosis by the GPR119 ligand, in an animal model having liver fibrosis induced by carbon tetrachloride ($CCl_4$), an effect of the GPR119 ligand on inhibiting liver fibrosis was observed.

Figure 3A:
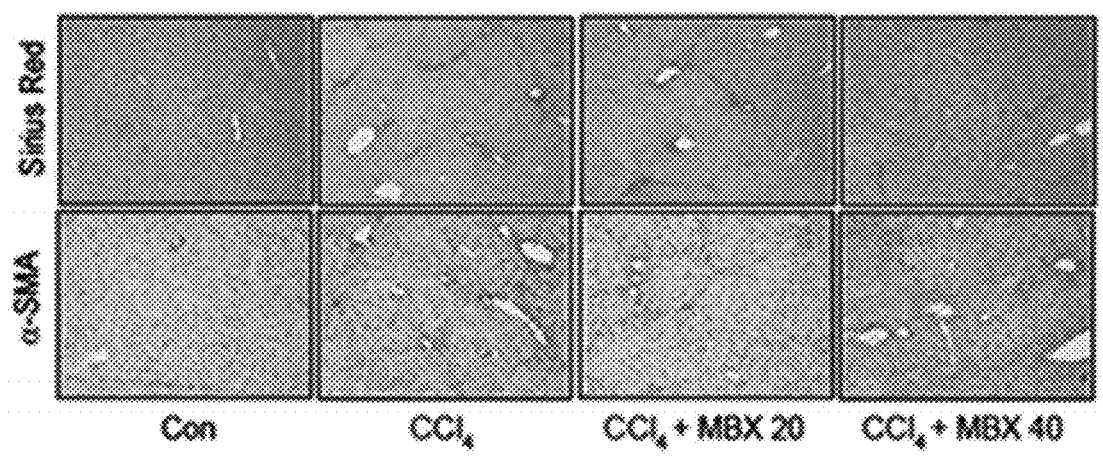
FIG. 3a illustrates the change of α-SMA expression by treatment with a GPR119 ligand in a liver fibrosis animal model.

First, 1 ml/kg of carbon tetrachloride was intraperitoneally administered twice a week, and also orally administered with the GPR119 ligand (MBX-2982) at doses of 20 and 40 mg/kg, respectively, once a day for 5 days a week. Three weeks later, liver tissue was extracted, subjected to sirius red staining for confirming collagen production and immunohistochemical staining for confirming expression of a HSC activation marker, that is, α-SMA, and then compared with a control group and a carbon tetrachloride only-treated group. Consequently, as shown in FIG. 3a, it was confirmed that collagen production elevated by treatment with carbon tetrachloride and increased α-SMA expression were significantly reduced in the group to which 40 mg/kg of the GPR119 ligand (MBX-2982) was administered.

Figure 3B:
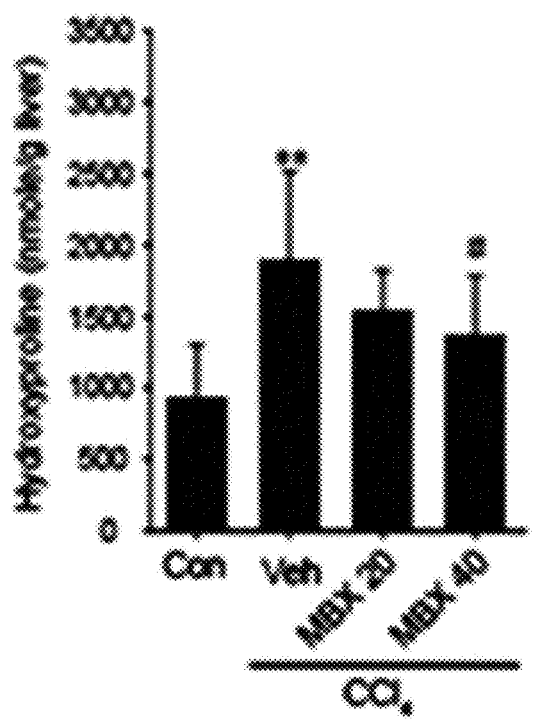
FIG. 3b illustrates the quantification of the main degradation product of collagen, hydroxyproline, in a liver fibrosis animal model.

Subsequently, the main degradation product of collagen, hydroxyproline, was quantified in each laboratory animal, and as a result, as shown in FIG. 3b, it was confirmed that an amount of hydroxyproline increased by the administration of the carbon tetrachloride was statistically significantly reduced in the group to which 40 mg/kg of the GPR119 ligand (MBX-2982) was administered.

Subsequently, ALT, AST, T-BIL and D-BIL in the blood of each group of laboratory animals were measured and compared. As a result, as shown in Table 4, it was confirmed that the blood ALT level elevated by the administration of the carbon tetrachloride was reduced by the administration of the GPR119 ligand.

TABLE 4

| Treatment | Veh | $CCl_4$ | $CCl_4$ + MBX 20 | $CCl_4$ + MBX 40 |
|---|---|---|---|---|
| ALT (U/L) | 14.07 ± 4.24 | 42.99 ± 7.90** | 38.55 ± 9.43 | 32.06 ± 5.17** |

TABLE 4-continued

| Treatment | Veh | CCl$_4$ | CCl$_4$ + MBX 20 | CCl$_4$ + MBX 40 |
|---|---|---|---|---|
| AST (U/L) | 56.67 ± 15.85 | 93.25 ± 38.08* | 94.06 ± 19.29 | 68.11 ± 21.55 |
| T-BIL (mg/dl) | 0.15 ± 0.02 | 0.23 ± 0.07** | 0.20 ± 0.05 | 0.23 ± 0.05 |
| D-BIL (mg/dl) | 0.06 ± 0.01 | 0.15 ± 0.05** | 0.11 ± 0.03 | 0.12 ± 0.04 |

Figure 3C:
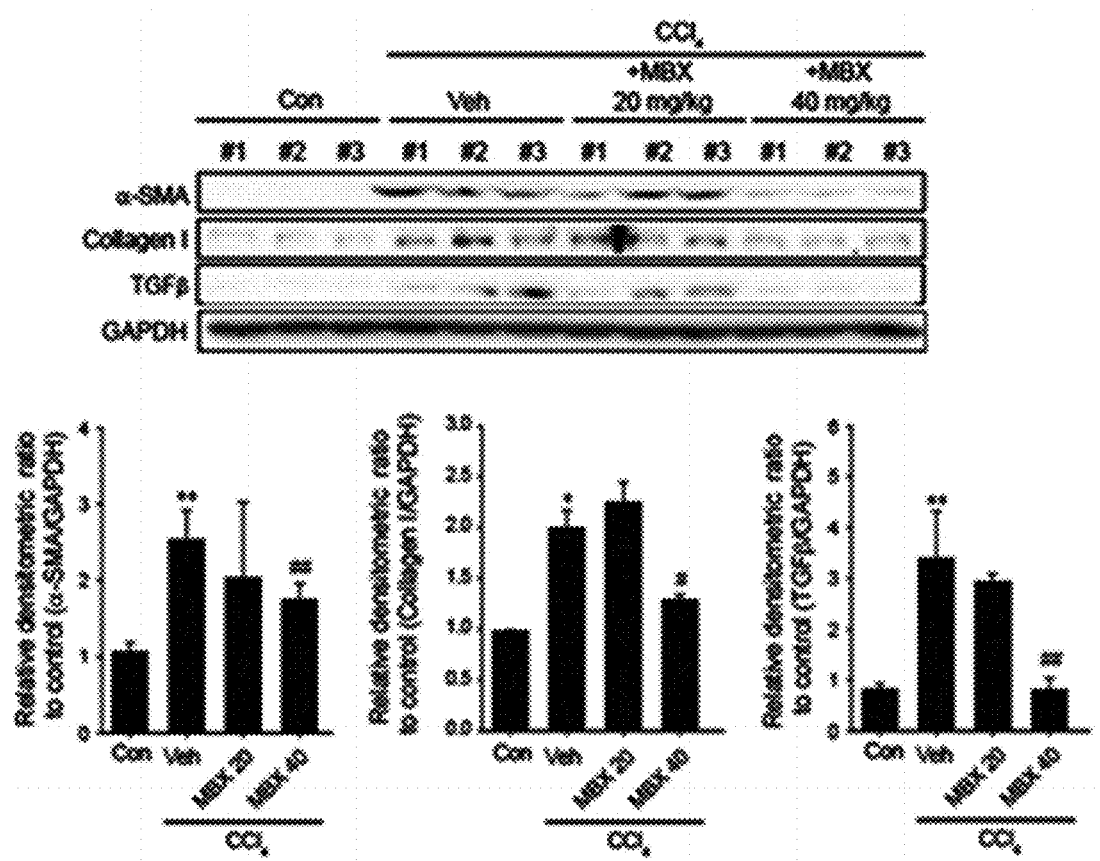
FIG. 3c illustrates the changes of expression of collagen I, TGFβ and α-SMA proteins by treatment with a GPR119 ligand in a liver fibrosis animal model.

Thereafter, changes in expression of collagen I, TGFβ and α-SMA proteins in liver tissue of each group of laboratory animals were examined by the method described in H. As a result, as shown in FIG. 3c, it was confirmed that in the fibrosis group induced by carbon tetrachloride administration, the expression of the collagen I, TGFβ and α-SMA proteins was increased, but in the group to which 40 mg/kg of the GPR119 ligand (MBX-2982) was administered, expression of collagen I, TGFβ and α-SMA was statistically significantly inhibited.

Example 4. Examination of Effect of GPR119 Ligand on AMPK Activation

To identify a signaling mechanism for the inhibitory effect of the GPR119 ligand on liver fibrosis, activation of a GPR119 signaling pathway, which is cAMP/PKA (cyclic AMP/Protein kinase A), was observed.

Figure 4A:
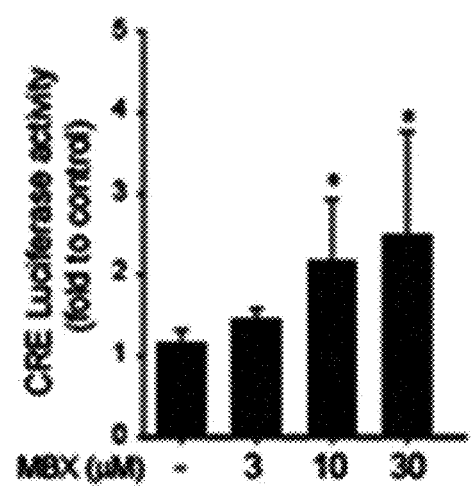
FIG. 4a illustrates changes in the action of a GPR119 ligand by the treatment with a PKA inhibitor, H-89.
Figure 4A:
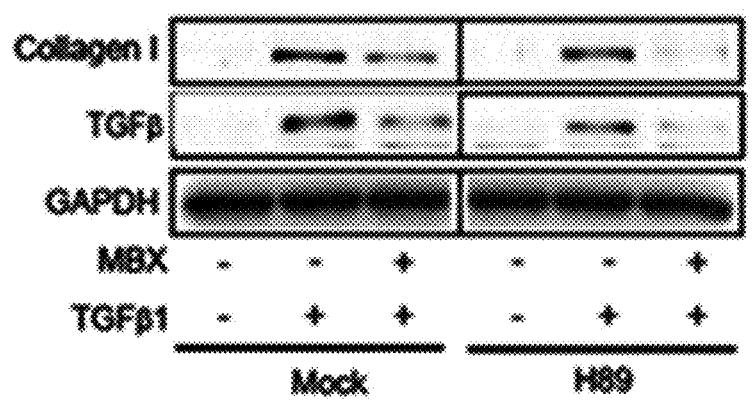

First, when a PKA inhibitor H-89 was treated, a change in action of the GPR119 ligand was examined. As a result, as shown in FIG. 4a, cAMP activation by the GPR119 ligand (MBX-2982) was observed, but the action of the GPR119 ligand on inhibiting collagen I and TGFβ expression was not offset when the PKA inhibitor H-89 was treated.

Figure 4B:
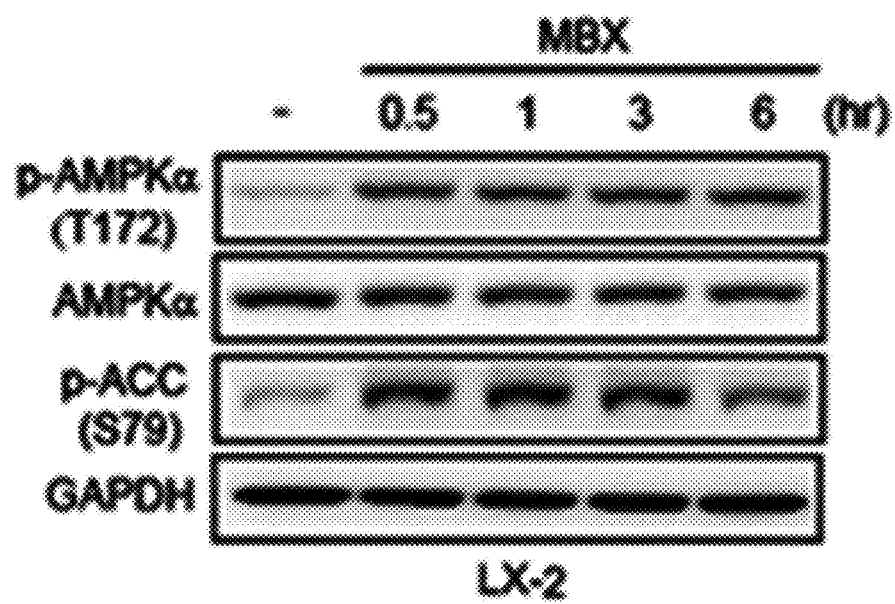
FIG. 4b illustrates AMPK activation by treatment of a human HSC line LX-2 with a GPR119 ligand.

It has been reported that AMPK activation inhibited HSC differentiation and collagen accumulation. The human HSC line LX-2 cultured by method D was treated with the GPR119 ligand, and the change in protein expression according to time was examined by the method described in H. As a result, as shown in FIG. 4b, it was confirmed that, when the GPR119 ligand (MBX-2982) was time-dependently treated, AMPK was highly activated (AMPK and ACC phosphorylation).

Figure 4C:
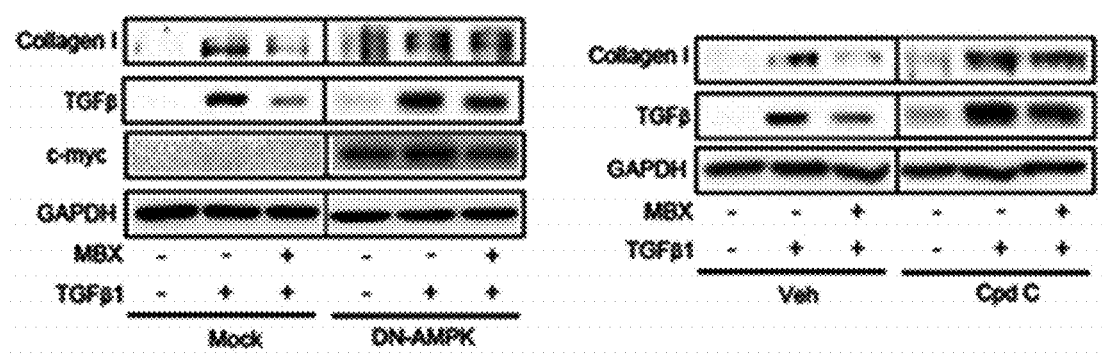
FIG. 4c illustrates treatment with an AMPK inhibitor, compound C, the transduction of DN-AMPK, and changes in the expression of TGFβ1-inducible liver fibrosis inducing factor (collagen I, TGFβ)
Figure 4D:
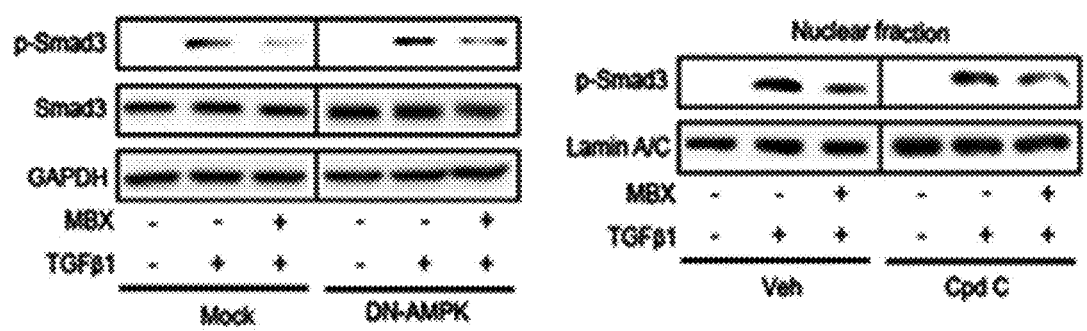
FIG. 4d illustrates treatment with an MPK inhibitor, compound C, the transduction of DN-AMPK, and changes in inhibition of a GPR119 ligand by TSmad3 phosphorylation.

Subsequently, an AMPK inhibitor, compound C, was treated and DN-AMPK was transduced, and a change in expression of TGFβ1-inducible liver fibrosis inducing factors (collagen I, TGFβ) was examined by the method described in H. As a result, as shown in FIG. 4c, it was confirmed that an inhibitory effect of the GPR119 ligand (MBX-2982) on expression was observed. However, as shown in FIG. 4d, the inhibitory action of the GPR119 ligand (MBX-2982) on the phosphorylation of Smad3 activated by TGFβ1 was partially recovered by AMPK inhibition, but not completely offset.

Figure 4E:
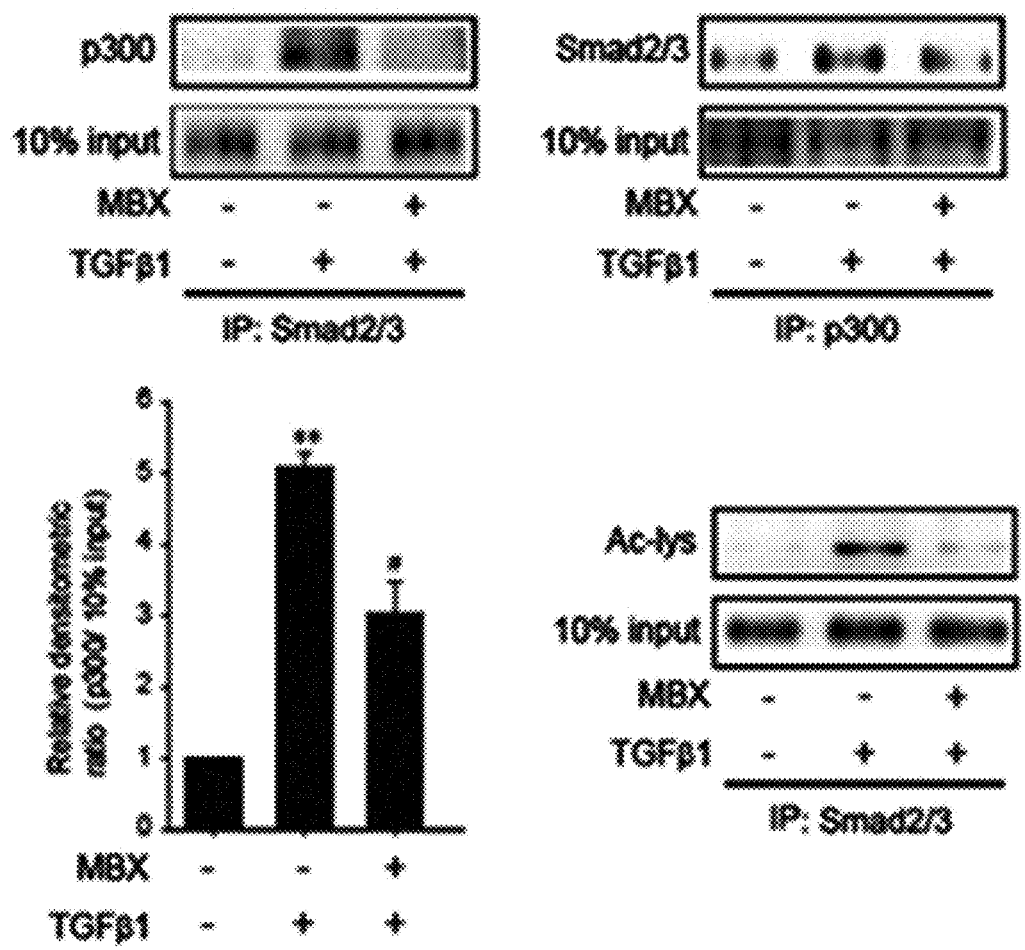
FIG. 4e illustrates interactions between Smad3 and p300 and Smad3 acetylation by treatment of a human HSC line LX-2 with a GPR119 ligand.

According to existing reports, AMPK activation in HSCs inhibits the interaction between Smad3 and p300 and inhibits the expression of a liver fibrosis-inducing factor through elevation of proteasomal degradation of the transcriptional coactivator p300. Thus, the influence of the GPR119 ligand on the interaction between Smad2/Smad3 and p300 was examined. To this end, in the human HSC line LX-2 cultured by the method of D, the interaction between Smad3 and p300 and Smad3 acetylation according to the GPR119 ligand treatment were examined, and as shown in FIG. 4e, when the GPR119 ligand (MBX-2982) was treated, it was confirmed that the interaction between Smad3 and p300 and Smad3 acetylation, which were elevated by TGFβ1, were considerably inhibited.

Figure 4F:
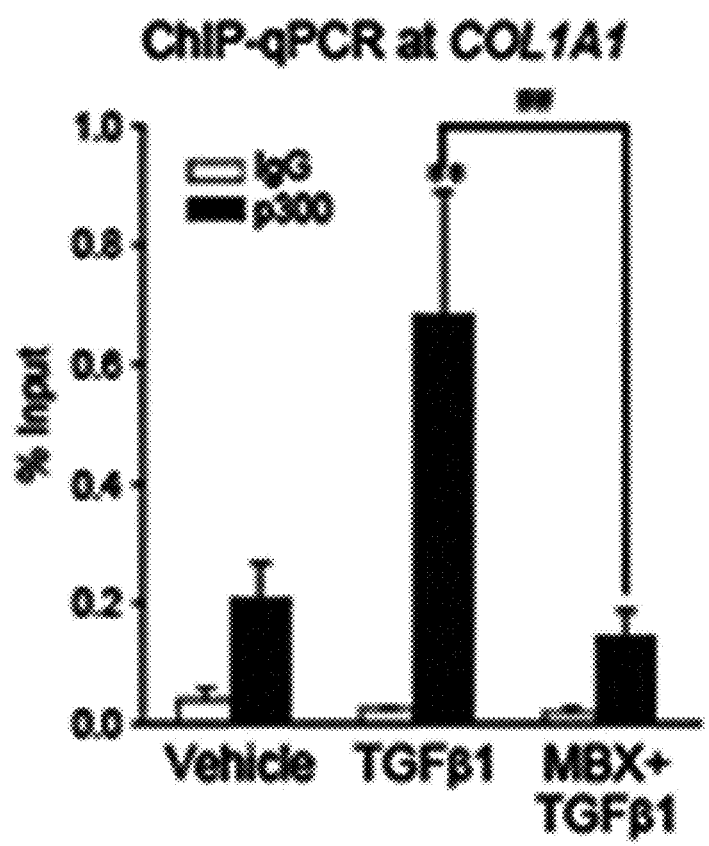
FIG. 4f illustrates binding between a promoter of a col1A1 gene and p300 is inhibited by the treatment with a GPR119 ligand through ChIP analysis.

Subsequently, the ChIP analysis performed by the method in L demonstrated that, as shown in FIG. 4f, when TGFβ1 was treated, binding between a promoter of the collA1 gene and p300 was inhibited by the treatment with the GPR119 ligand.

Figure 4G:
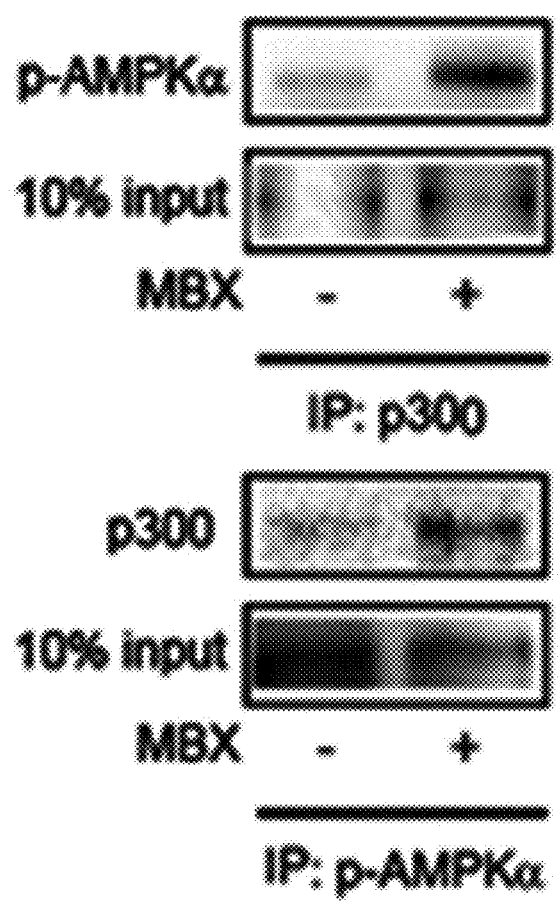
FIG. 4g illustrates that, when a human HSC line LX-2 is treated with a GPR119 ligand alone, activated AMPK is directly bound to p300, and thus AMPK activation has an influence on the interaction between p300 and Smad.

Subsequently, in the present invention, a mechanism for inhibiting the Smad-p300 interaction due to AMPK activation was investigated. To this end, when LX-2 cells were treated with GPR119 ligand (MBX-2982) alone, as shown in FIG. 4g, it was confirmed that the activated AMPK directly bound to p300. From the above result, it was seen that the AMPK activation had an influence on the interaction between p300 and Smad.

Figure 4H:
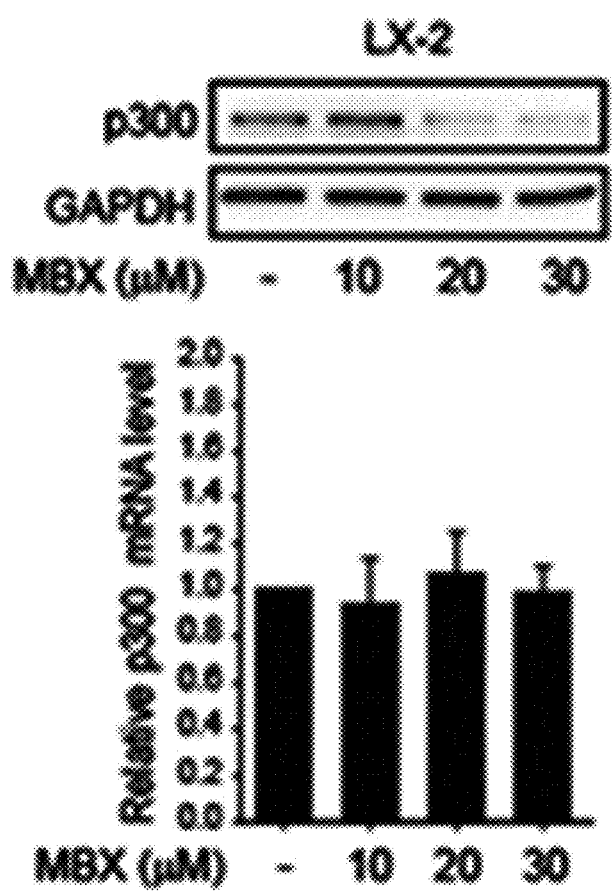
FIG. 4h illustrates changes in mRNA expression of p300 by treatment of a human HSC line LX-2 with a GPR119 ligand.
Figure 4I:
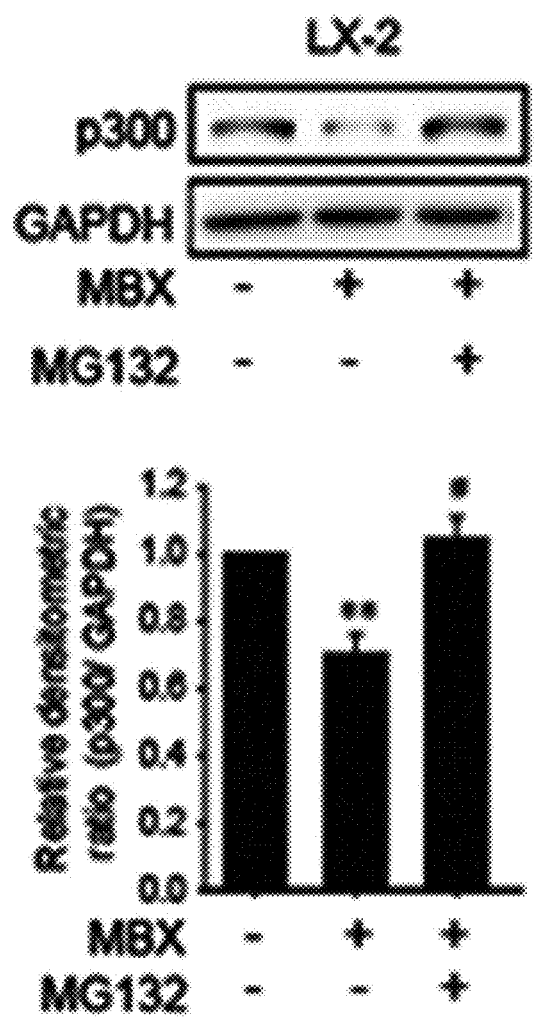
FIG. 4i illustrates a decrease in p300 protein expression by a GPR119 ligand is caused by proteasomal degradation.

Thereafter, in the present invention, the influence of the GPR119 ligand on p300 expression was observed. To this end, when the LX-2 cells were treated with the GPR119 ligand (MBX-2982) alone, as shown in FIG. 4h, it was confirmed that the expression of the p300 protein has reduced depending on the concentration of the GPR119 ligand (MBX-2982), and there was no influence on mRNA expression of p300. From the result, it was assumed that a decrease in the expression of the p300 protein due to the GPR119 ligand could be caused by proteasomal degradation, and therefore the expression of the p300 protein was observed using a proteasome inhibitor, which is MG132. Consequently, as shown in FIG. 4i, it was confirmed that expression of the p300 protein decreased by the treatment with the GPR119 ligand (MBX-2982) recovered with the MG132 treatment.

Example 5. Examination of the Inhibitory Effect of GPR119 Ligands on HSC Proliferation To confirm whether GPR119 ligands improves liver fibrosis, the effect of a GPR119 ligand on HSC proliferation observed in liver fibrosis was evaluated.

Figure 5A:
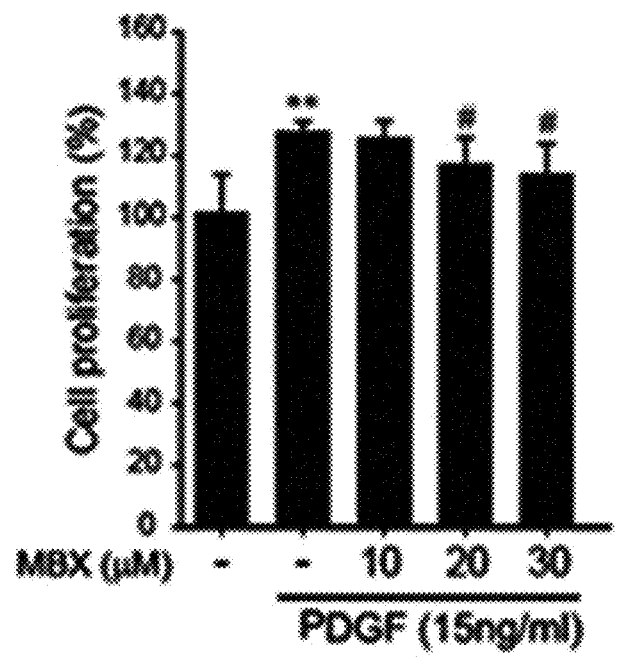
FIG. 5a illustrates inhibition of cell proliferation by treatment with a GPR119 ligand in HSCs in which cell proliferation is induced by PDGF introduction.

First, a platelet derived growth factor (PDGF) known as a potent growth factor for HSCs was introduced to induce HSC proliferation, and then the inhibitory effect of the GPR119 ligand (MBX-2982) thereon was examined. Consequently, as shown in FIG. 5a, when the HSC line LX-2 was treated with the GPR119 ligand (MBX-2982), it was confirmed that HSC proliferation induced by PDGF was inhibited.

Figure 5B:
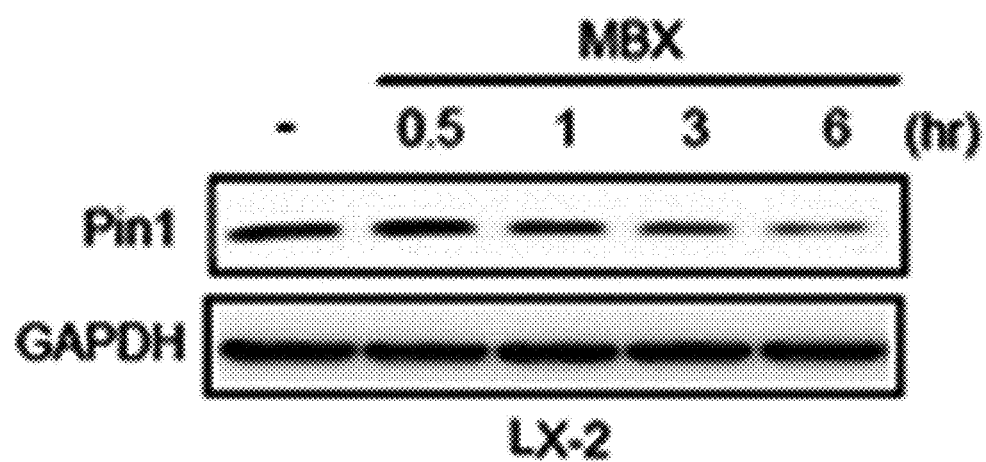
FIG. 5b illustrates changes in Pin1 expression according to the treatment of a human HSC line LX-2 with a GPR119 ligand.

According to existing reports, as a core factor participating in cell proliferation by PDGF, peptidyl prolyl isomerase (Pin1) is known. Therefore, Pin1 relevance with respect to the GPR119 ligand action was evaluated. To this end, as the result of examining a change in Pin1 expression according to the treatment with the GPR119 ligand (MBX-2982) in the LX-2 cells, as shown in FIG. 5b, it was confirmed that Pin1 expression was time-dependently reduced. This result shows that the inhibitory effect of GPR119 on HSC proliferation can mediate regulation of Pin1 expression.

Figure 5C:
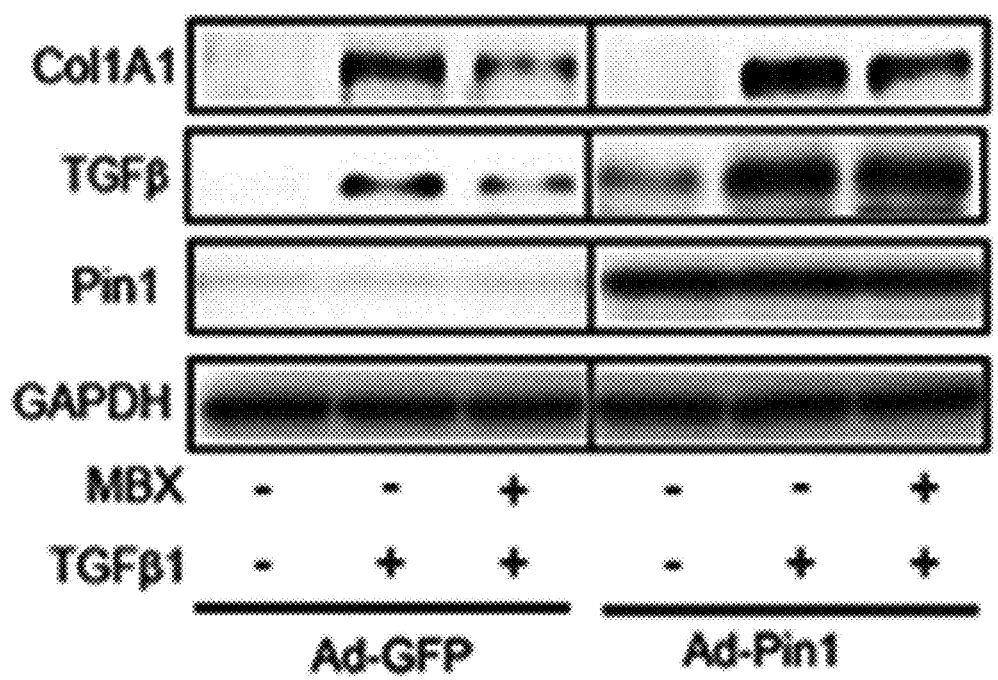
FIG. 5c illustrates the inhibitory effects of a GPR119 ligand on TGFβ1-inducible collagen I and TGFβ expression due to transduction of a Pin1 adenovirus into a human HSC line LX-2.

It has been reported that Pin1 is involved in Smad2/3 protein stabilization, which is activated by the produced TGFβ1, and metastasis and infiltration of prostate cancer induced by TGFβ1. Therefore, the inhibitory effect of the GPR119 ligand on expression of TGFβ1-inducible collagen I and TGFβ was confirmed by transducing a Pin1 adenovirus into the HSC line LX-2. Consequently, as shown in FIG. 5c, it was confirmed that the inhibitory effect of the GPR119 ligand (MBX-2982) on collagen I and TGFβ expression was reversed due to the overexpression of Pin1.

It should be understood by those of ordinary skill in the art that the above descriptions of the present invention are exemplary, and the example embodiments disclosed herein can be easily modified into other specific forms without changing the technical spirit or essential features of the present invention. Therefore, it should be interpreted that the example embodiments described above are exemplary in all aspects, and are not limitative.

The invention claimed is:

1. A method for treating liver fibrosis by administering a pharmaceutically acceptable amount of a pharmaceutical composition comprising a G protein coupled receptor 119 (GPR119) ligand as an active ingredient to an individual, wherein the GPR 119 ligand is 4-((4-(1H-tetrazol-1-yl)phenoxy)methyl)-2-(1-(5-ethyl-pyrimidin-2-yl)piperidin-4-yl)thiazole (MBX2982) or 3-isopropyl-5-(4-(((6-(4-(methylsulfonyl)phenyl)pyridin-3-yl)oxy)methyl)piperidin-1-yl)-1,2,4-oxadiazole (GSK1292263).

2. The method of claim 1, wherein the GPR119 ligand inhibits hepatic stellate cell (HSC) proliferation.

3. The method of claim 1, wherein the GPR119 ligand inhibits HSC activation.

4. The method of claim 1, wherein the GPR119 ligand enhances the activity of AMP-activated protein kinase (AMPK).

5. The method of claim 1, wherein the GPR119 ligand inhibits collagen I expression.

6. The method of claim 1, wherein the GPR119 ligand inhibits the expression of transforming growth factor β (TGFβ).

7. The method of claim 1, wherein the GPR119 ligand inhibits the expression of α-smooth muscle actin (α-SMA).

* * * * *

```
                            SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: mouse GPR119 forward primer

<400> SEQUENCE: 1
tgtcctaacc atcctcatca                                                  20

<210> SEQ ID NO 2
<211> LENGTH: 18
<212> TYPE: DNA
<213> ORGANISM: Artificial Sequence
<220> FEATURE:
<223> OTHER INFORMATION: mouse GPR119 reverse primer

<400> SEQUENCE: 2
atagccacgc caatcaag                                                    18

<210> SEQ ID NO 3
<211> LENGTH: 20
<212> TYPE: DNA
<213> ORGANISM: Artificial Sequence
<220> FEATURE:
<223> OTHER INFORMATION: mouse S18r forward primer

<400> SEQUENCE: 3
gtaacccgtt gaaccccatt                                                  20

<210> SEQ ID NO 4
<211> LENGTH: 20
<212> TYPE: DNA
<213> ORGANISM: Artificial Sequence
<220> FEATURE:
<223> OTHER INFORMATION: mouse S18r reverse primer

<400> SEQUENCE: 4
ccatccaatc ggtagtagcg                                                  20

<210> SEQ ID NO 5
<211> LENGTH: 20
<212> TYPE: DNA
<213> ORGANISM: Artificial Sequence
<220> FEATURE:
<223> OTHER INFORMATION: human GPR119 forward primer

<400> SEQUENCE: 5
ggctgtggtt agtgtcttac                                                  20

<210> SEQ ID NO 6
<211> LENGTH: 20
<212> TYPE: DNA
<213> ORGANISM: Artificial Sequence
<220> FEATURE:
<223> OTHER INFORMATION: human GPR119 reverse primer

<400> SEQUENCE: 6
acgaagtgag ggtgaaatac                                                  20
```

-continued

<210> SEQ ID NO 7
<211> LENGTH: 20
<212> TYPE: DNA
<213> ORGANISM: Artificial Sequence
<220> FEATURE:
<223> OTHER INFORMATION: human S16r forward primer

<400> SEQUENCE: 7
tccaagggtc cgctgcagtc                                              20

<210> SEQ ID NO 8
<211> LENGTH: 22
<212> TYPE: DNA
<213> ORGANISM: Artificial Sequence
<220> FEATURE:
<223> OTHER INFORMATION: human S16r reverse primer

<400> SEQUENCE: 8
cgttcacctt gatgagccca tt                                           22

<210> SEQ ID NO 9
<211> LENGTH: 24
<212> TYPE: DNA
<213> ORGANISM: Artificial Sequence
<220> FEATURE:
<223> OTHER INFORMATION: mouse col1A1 forward primer

<400> SEQUENCE: 9
actgcaacat ggagacaggt caga                                         24

<210> SEQ ID NO 10
<211> LENGTH: 24
<212> TYPE: DNA
<213> ORGANISM: Artificial Sequence
<220> FEATURE:
<223> OTHER INFORMATION: mouse col1A1 reverse primer

<400> SEQUENCE: 10
atcggtcatg ctctctccaa acca                                         24

<210> SEQ ID NO 11
<211> LENGTH: 25
<212> TYPE: DNA
<213> ORGANISM: Artificial Sequence
<220> FEATURE:
<223> OTHER INFORMATION: mouse TGFbeta1 forward primer

<400> SEQUENCE: 11
cttcagctcc acagagaaga actgc                                        25

<210> SEQ ID NO 12
<211> LENGTH: 25
<212> TYPE: DNA
<213> ORGANISM: Artificial Sequence
<220> FEATURE:
<223> OTHER INFORMATION: mouse TGFbeta1 reverse primer

<400> SEQUENCE: 12
cacgatcatg ttggacaact gctcc                                        25

<210> SEQ ID NO 13
<211> LENGTH: 19
<212> TYPE: DNA
<213> ORGANISM: Artificial Sequence
<220> FEATURE:

<223> OTHER INFORMATION: human TGFbeta1 forward primer

<400> SEQUENCE: 13
cccagcatct gcaaagctc                                                19

<210> SEQ ID NO 14
<211> LENGTH: 20
<212> TYPE: DNA
<213> ORGANISM: Artificial Sequence
<220> FEATURE:
<223> OTHER INFORMATION: human TGFbeta1 reverse primer

<400> SEQUENCE: 14
gtcaatgtac agctgccgca                                               20

<210> SEQ ID NO 15
<211> LENGTH: 23
<212> TYPE: DNA
<213> ORGANISM: Artificial Sequence
<220> FEATURE:
<223> OTHER INFORMATION: human col1A1 forward primer

<400> SEQUENCE: 15
aacatgacca aaaccaaaa gtg                                            23

<210> SEQ ID NO 16
<211> LENGTH: 22
<212> TYPE: DNA
<213> ORGANISM: Artificial Sequence
<220> FEATURE:
<223> OTHER INFORMATION: human col1A1 reverse primer

<400> SEQUENCE: 16
cattgtttcc tgtgtcttct gg                                            22

<210> SEQ ID NO 17
<211> LENGTH: 21
<212> TYPE: DNA
<213> ORGANISM: Artificial Sequence
<220> FEATURE:
<223> OTHER INFORMATION: rat TGFbeta1 forward primer

<400> SEQUENCE: 17
tcgggagaga ggaggacttt g                                             21

<210> SEQ ID NO 18
<211> LENGTH: 20
<212> TYPE: DNA
<213> ORGANISM: Artificial Sequence
<220> FEATURE:
<223> OTHER INFORMATION: rat TGFbeta1 reverse primer

<400> SEQUENCE: 18
ggcttgcgac ccacgtagta                                               20

<210> SEQ ID NO 19
<211> LENGTH: 20
<212> TYPE: DNA
<213> ORGANISM: Artificial Sequence
<220> FEATURE:
<223> OTHER INFORMATION: rat GAPDH forward primer

<400> SEQUENCE: 19
agatccacaa cggatacatt                                               20

```
<210> SEQ ID NO 20
<211> LENGTH: 20
<212> TYPE: DNA
<213> ORGANISM: Artificial Sequence
<220> FEATURE:
<223> OTHER INFORMATION: rat GAPDH reverse primer

<400> SEQUENCE: 20
tccctcaaga ttgtcagcaa                                                    20

<210> SEQ ID NO 21
<211> LENGTH: 20
<212> TYPE: DNA
<213> ORGANISM: Artificial Sequence
<220> FEATURE:
<223> OTHER INFORMATION: p300 forward primer

<400> SEQUENCE: 21
cattcccagc tcccctctct                                                    20

<210> SEQ ID NO 22
<211> LENGTH: 20
<212> TYPE: DNA
<213> ORGANISM: Artificial Sequence
<220> FEATURE:
<223> OTHER INFORMATION: p300 reverse primer

<400> SEQUENCE: 22
agtctacgtg gcaggcaagg                                                    20
```